United States Patent [19]

Heng

[11] Patent Number: 5,229,266
[45] Date of Patent: Jul. 20, 1993

[54] ASSAY OF HAIR REGROWTH MARKER

[76] Inventor: Madalene C. Y. Heng, 17632 Vincennes St., Northridge, Calif. 91325

[21] Appl. No.: 740,286

[22] Filed: Aug. 5, 1991

[51] Int. Cl.$^5$ ............................................. G01N 33/554
[52] U.S. Cl. ....................................... 435/7.2; 435/7.5; 435/7.9; 435/7.92; 436/501; 436/536; 436/827
[58] Field of Search .................... 435/7.5, 7.9, 7.92, 435/960, 975, 964, 7.2, 827, 960; 436/815, 87, 536, 501, 536, 827; 530/387, 388.1

[56] References Cited

U.S. PATENT DOCUMENTS 4,684,609  8/1987  Hsu .......................................... 435/7

OTHER PUBLICATIONS

Ku, W. W. and Bernstein, I. "Lectin Binding as a Probe of Proliferative and Differentiative Phases in Primary Monolayer Cultures of Cutaneous Keratinocytes". *Exp. Cell. Res.* vol. 175, (1988) pp. 298–316.

S. J. Kleinschuster & A. A. Moscona, "Interaction of Embryonic and Fetal Neural Retina Cells with Carbohydrate-Binding Phytoagglutinins; Cell Surface Changes with Differentiation", *Exp. Cell Res.* 70:397–410 (1970).

R. Lallier, "Effects of Concanavalin A on the Development of Sea Urchin Egg", *Exp. Cell Res.* 72:157–163 (1972).

Y. Matsushita et al., "Carcinoma-Specific *Ulex europaeus* Agglutin-I binding Glycoproteins of Human Colorectal Carcinoma and Its Relation to Carcinoembryonic Antigen", *J. Natl. Cancer Inst.* 75:219–226 (1985).

J. B. Hamilton, "Patterned Loss of Hair in Man: Types and Incidence", *Ann. N.Y. Acad. Sci.* 53:708–728 (1951).

G. S. Bazzano, "Topical Tretinoin for Hair Growth Promotion", *J. Am. Acad. Dermatol.* 15:890–893 (1986).

N. K. Nemanic et al., "Alterations in Membrane Sugars During Epidermal Differentiation: Visualization with Lectins and Role of Glycosidases", *J. Histochem. Cytochem.* 31:887–897 (1983).

(List continued on next page.)

*Primary Examiner*—Mary E. Ceperley
*Assistant Examiner*—S. K. Reilly
*Attorney, Agent, or Firm*—Michael B. Farber; Sarah B. Adriano

[57] ABSTRACT

Terminal hair follicles of the human scalp in the anagen phase of growth are distinguished from non-terminal follicles or from terminal follicles in phases of growth other than anagen by the presence of L-fucose on the cell membranes of the infrainfundibular portion of suprabasal keratinocytes of the follicles. L-fucose can be detected by a lectin specific for it. Accordingly, a method for identifying terminal hair follicles in the anagen phase of growth in the human scalp comprises the steps of: (1) contacting the cell membrane of the infrainfundibular portion of suprabasal keratinocytes with a lectin capable of specifically binding L-fucose on the cell membrane of the infrainfundibular portion of the keratinocytes; and (2) identifying terminal hair follicles by determining the lectin bound, the lectin preferentially binding to terminal hair follicles in the anagen phase of growth as opposed to terminal hair follicles in phases of growth other than anagen or non-terminal hair follicles. The lectin is preferably *Ulex europaeus* lectin I. Preferably, the lectin is biotinylated and detected through use of a label conjugate comprising a substance specific for biotin conjugated to a detectable label, the substance specific for biotin being selected from the group consisting of avidin and an anti-biotin antibody. The method can be adapted to determine the effectiveness of a drug for therapy of androgenetic alopecia.

23 Claims, 4 Drawing Sheets

OTHER PUBLICATIONS

R. J. Wieser & F. Oesch, "Contact-Dependent Regulation of Growth of Diploid Human Fibroblasts is Dependent on the Presence of Terminal Galactose Residues on Plasma Membrane Glycoproteins", *Exp. Cell Res.* 176–180 (1988).

S. Fleming & G. Brown, "The Expression of 3-Fucosylated-N-Acetyl Lactosamine Carbohydrate Determinates in Renal Tumors", *Histopathology* 11:171–182 (1987).

I. Virtanen et al., "Population Heterogeneity in the Surface Expression of *Ulex europaeus* I-Lectin (UEA I)-Binding Sites in Cultured Malignant and Transformed Cells", *Exp. Cell Res.* 161:53–62 (1985).

N. L. Nieland, "Epidermal Intercellular Staining with Fluorescein-Conjugated Phytohemagglutinins", *J. Invest. Dermatol.* 60:61–66 (1973).

R. K. Brabec et al., "Differential Lectin Binding to Cellular Membranes in the Epidermis of the Newborn Rat", *Proc. Natl. Acad. Sci. USA* 77:477–479 (1980).

N. K. Nemanic & P. N. Elias, "Localization and Identification of Sugars in Mannalian Epidermis", *J. Cell. Biol.* 83:46A (1979).

J. Petryniak & I. J. Goldstein, "Immunochemical Studies on the Interaction Between Synthetic Glycoconjugates and α-L-Fucosyl Binding Lectins", *Biochemistry* 25:2829–2838 (1986).

R. Brown et al., "Changes in Lectin Binding by Differentiating Cutaneous Keratinocytes from the Newborn Rat", *J. Invest. Dermatol.* 88:719–726 (1987).

J. D. Zieske & I. A. Bernstein, "Modification of Cell Surface Glycoprotein: Addition of Fucosyl Residues During Epidermal Differentiation", *J. Cell Biol.* 95:66–631 (1982).

P. R. Mann et al., "Distribution of Glycoproteins Containing Fucose in Normal and Psoriatic Keratinocytes", *Br. J. Dermatol.* 102:649–657 (1980).

J. M. Gommans et al., "Studies on the Plasma Membrane of Normal and Psoriatic Keratinocytes. 5. Lectin Binding", *Br. J. Dermatol.* 106:317–322 (1982).

W. T. Bergfeld, "Etiology and Diagnosis of Androgenetic Alopecia", *Clin. Dermatol.* 6:102–107 (1988).

T. A. Tromovitch et al., "Medical Treatment of Male Pattern Alopecia (Androgenic Alopecia)", *Head & Neck Surg.* 7:336–339 (1985).

E. A. Olsen et al., "Topical Minoxidil in Early Male Pattern Baldness", *J. Am. Acad. Dermatol.* 13:185–192 (1985).

ASSAY OF HAIR REGROWTH MARKER

BACKGROUND

Baldness, especially male pattern baldness (androgenetic alopecia), although not a disabling or life-threatening condition, is of great importance to those affected by it. The loss of hair is a psychological trauma for many men. For hundreds of years, people have sought cures for baldness, but only recently with the development of minoxidil and retinoic acid, have treatments of some effectiveness emerged.

The continued development of effective treatments for baldness has led to the need for a rapid and efficient means of screening the effect of prospective anti-baldness medications. At present, such drugs must be tested by the manual method of counting hairs in order to determine hair growth, which requires large numbers of patients for statistical significance. This is very time consuming as well as subject to error. Accordingly, there is a need for a faster and more efficient way of assessing hair growth and determining the effect of a medication or drug on hair growth, particularly for treatment of androgenetic alopecia.

SUMMARY

I have developed a method of identifying terminal hair follicles in the anagen phase, distinguishing them from: (i) terminal follicles in other than the anagen phase or (ii) non-terminal hair follicles. This allows me to determine the effectiveness of a drug for therapy of androgenetic alopecia.

A method according to the present invention for identifying terminal hair follicles in the anagen phase of growth in the human scalp, the suprabasal keratinocytes of the follicles having distinguishable infundibular and infrainfundibular portions, comprises the steps of:

(1) contacting the cell membrane of the infrainfundibular suprabasal keratinocytes with a lectin capable of specifically binding L-fucose on the cell membrane of the infrainfundibular keratinocytes; and (2) identifying terminal hair follicles by determining the lectin bound, the lectin preferentially binding to terminal hair follicles in the anagen phase of growth as opposed to terminal hair follicles in phases of growth other than anagen or non-terminal hair follicles.

The lectin can be selected from the group consisting of *Lotus tetragonolobus* lectin I, *L. tetragonolobus* lectin II, *L. tetragonolobus* lectin III, *Ulex europaeus* lectin I, and *Anguilla rostrata* lectin. Preferably, the lectin is *Ulex europaeus* lectin I.

Preferably the lectin is biotinylated, and the step of determining the lectin bound can then comprise contacting the cell membrane with a label conjugate comprising a substance specific for biotin conjugated to a detectable label, the substance specific for biotin being selected from the group consisting of avidin and an anti-biotin antibody. Preferably, the substance specific for biotin is avidin.

The detectable label can be selected from the group consisting of radioactive labels, fluorescent labels, colorimetric labels, and enzyme labels. Preferably, the detectable label is an enzyme label, most preferably horseradish peroxidase.

In a less preferred alternative, the lectin can be directly conjugated to a detectable label.

Another aspect of the invention is a kit for the identification of terminal hair follicles in the anagen phase of growth in the human scalp. The kit employs a biotinylated lectin and a substance specific for biotin, as discussed above, and comprises:

(1) a biotinylated lectin capable of specifically binding L-fucose on the cell membrane of the infrainfundibular suprabasal keratinocytes;

(2) a label conjugate comprising a substance specific for biotin conjugated to a detectable label, the substance specific for biotin being selected from the group consisting of avidin and an anti-biotin antibody; and (3) means for detecting the label.

Yet another aspect of the invention is a method for determining the effectiveness of a drug for therapy of androgenetic alopecia. The method can be applied to an individual patient or multiple patients; in the former case, different regions of the scalp are compared. When an individual patient is used, the method comprises the steps of:

(1) selecting a patient an area of whose scalp is affected by androgenetic alopecia;

(2) treating only a first region of the area of the scalp affected by androgenetic alopecia with a known dosage of the drug while leaving a second region untreated;

(3) for suprabasal keratinocytes of the follicles having distinguishable infundibular and infrainfundibular portions, contacting the suprabasal keratinocyte cell membrane of the infrainfundibular portion of the first and second regions with a lectin capable of specifically binding L-fucose on the cell membrane of the infrainfundibular portion of the keratinocytes; and (4) comparing the binding of the lectin to the infrainfundibular portion of suprabasal keratinocytes in the first and second regions to determine the effectiveness of the drug at the dosage administered.

The step of comparing the binding of the lectin to the suprabasal keratinocytes of the infrainfundibular portions in the first and second regions can comprise determining the quantity of lectin bound per suprabasal keratinocyte in the first and second regions. The difference between the quantity of lectin bound per suprabasal keratinocyte in the first and second regions is a measure of the effectiveness of the drug.

When multiple patients are used, the method comprises:

(1) selecting at least two patients, areas of whose scalps are affected by androgenetic alopecia;

(2) treating a region of the area of the scalp affected by androgenetic alopecia of at least one patient with the drug at a known dosage;

(3) leaving a corresponding region of the area of the scalp affected by androgenetic alopecia of at least one patient untreated;

(4) for suprabasal keratinocytes of the follicles having distinguishable infundibular and infrainfundibular portions, contacting the cell membrane of the infrainfundibular suprabasal keratinocytes in the region of the scalps of the treated and untreated patients with a lectin capable of specifically binding L-fucose on the cell membrane of the infrainfundibular keratinocytes; and (5) comparing the binding of the lectin to the infrainfundibular suprabasal keratinocytes in the region for treated and untreated patients to determine the effectiveness of the drug at the dosage administered.

The present invention further comprises a method of identifying terminal hair follicles in the anagen phase of growth based on the length of their infrainfundibular portions. Terminal follicles in the anagen phase of growth have significantly longer infrainfundibular portions than do terminal follicles in phases of growth other than anagen or non-terminal follicles. The method comprises:

(1) taking a scalp biopsy from the scalp on which terminal hair follicles in the anagen phase of growth are to be identified;

(2) preparing a longitudinal section from the biopsy;

(3) measuring the length of the infrainfundibular portion of a sufficient number of follicles in the section to obtain a distribution of lengths of the infrainfundibular portion of the follicles and a mean value of the distribution; and (4) comparing the mean value of the distribution of follicle lengths with values characteristic of terminal follicles in the anagen phase and follicles other than terminal follicles in the anagen phase to identify terminal hair follicles in the anagen phase.

DRAWINGS

These and other features, aspects, and advantages of the present invention will become better understood with reference to the following description, appended claims, and the accompanying drawings where:

Figure 1A:
FIG. 1(a) shows a photomicrograph at 250× magnification of a frozen section treated with *Ulex europaeus* I lectin (UEA I) of a terminal hair occipital scalp follicle in early anagen, showing UEA I positivity of the bulbar follicular keratinocytes (single arrow) and perifollicular blood vessels (double arrows) and showing lack of UEA I binding to cells of the external root sheaths (triple arrows)
Figure 1B:
FIG. 1(b) is a photomicrograph at 250× magnification of a frozen section of a UEA I-treated terminal occipital follicle, showing an oblique section through the bulb at a more advanced stage of anagen than shown in FIG. 1(a), showing the UEA I positivity of keratinocytes of both the external root sheaths (double arrows) and internal root sheaths (single arrow)
Figure 1C:
FIG. 1(c) is a photomicrograph at 250× magnification of a frozen section of a UEA I-treated terminal occipital follicle in longitudinal section in the anagen phase, showing UEA I positivity of the infrainfundibular keratinocytes of both the external (single arrow) and internal (double arrows) root sheaths and showing numerous perifollicular blood vessels (triple arrows)
Figure 1D:
Figure 1E:
Figure 1F:
Figure 2A:
Figure 2B:
Figure 3:
Figure 4:
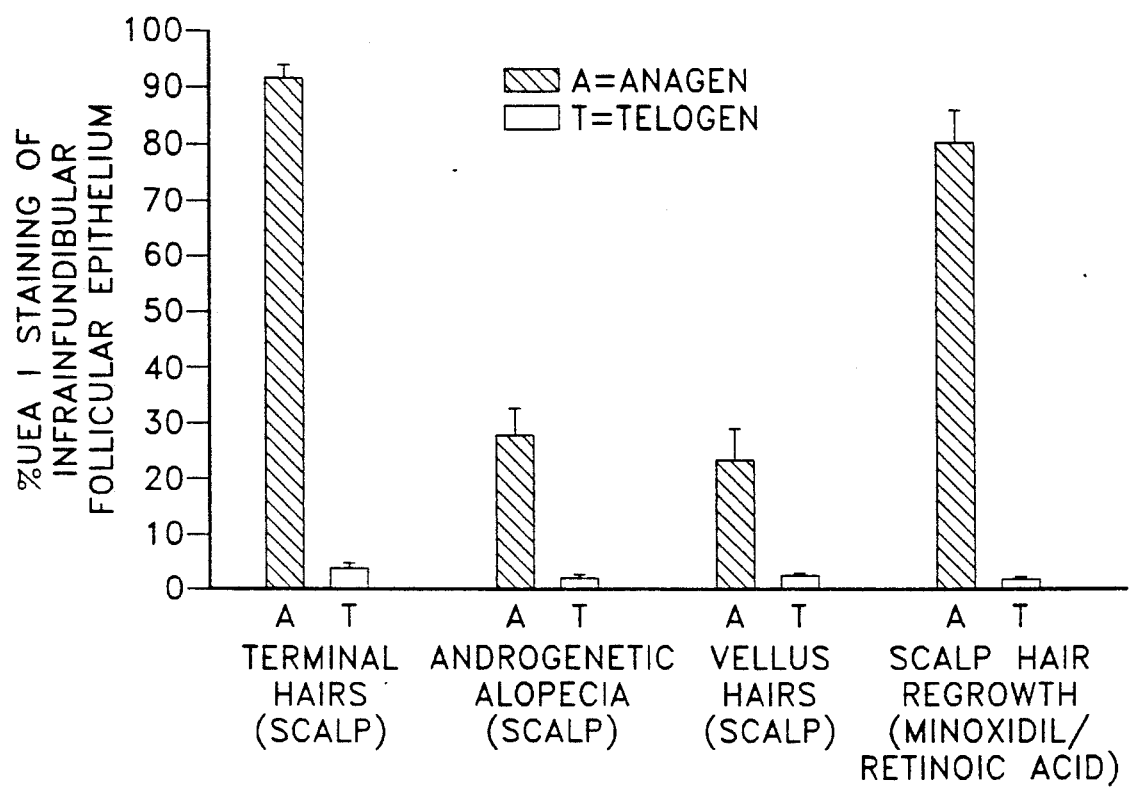
Figure 6:
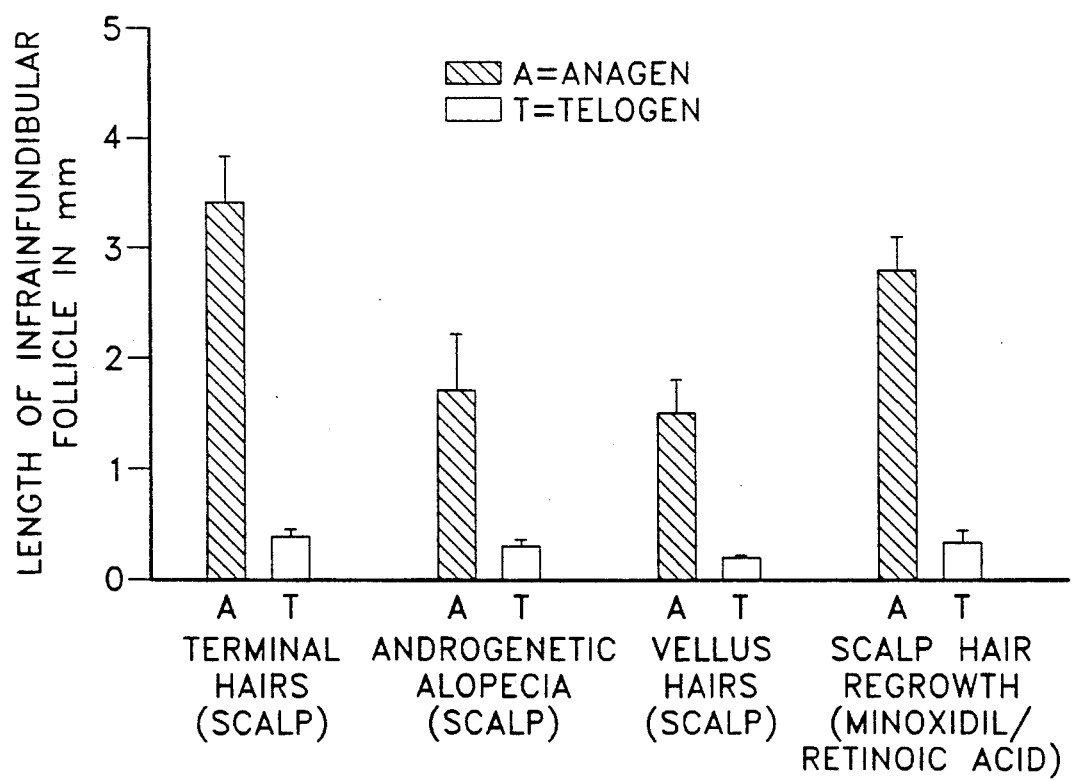
Figure 5A:
Figure 5B:
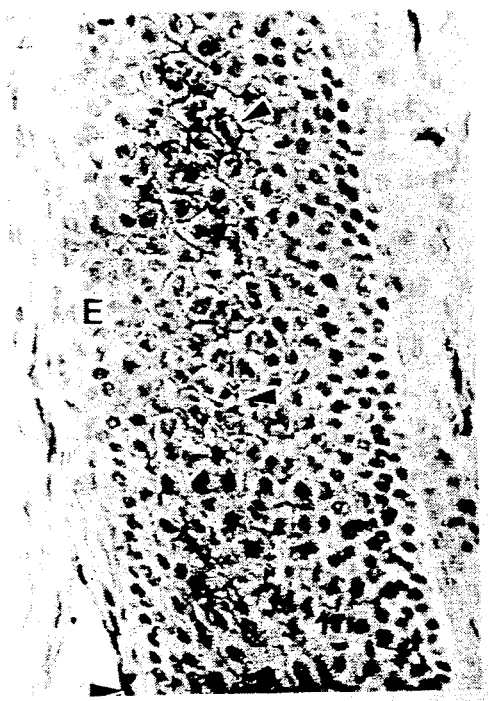

FIG. 1(d) is a photomicrograph at 250× magnification of a UEA I-treated terminal occipital follicle in early catagen, showing crimping of the internal root sheath which retains UEA I positivity (double arrows) and showing loss of UEA I from the infrainfundibular follicular keratinocytes of the external root sheaths (E), and also showing the presence of numerous perifollicular vessels (single arrow);

FIG. 1(e) is a photomicrograph at 150× magnification of a UEA I-treated terminal occipital scalp follicle in late catagen/early telogen with a shriveled bulb, showing loss of UEA I positivity from the infrainfundibular keratinocytes of the external root sheaths (E) and decreased staining of the internal root sheaths (double arrows);

FIG. 1(f) is a photomicrograph at 250× magnification of a UEA I-treated terminal occipital scalp follicle in telogen situated at the level of the sebaceous glands (S), with minimal UEA I positivity of the internal root sheaths (single arrow), and essentially negative UEA I binding in the external root sheaths (E), while blood vessels (double arrows) are UEA I positive;

FIG. 2(a) is a photomicrograph at 250× magnification of a UEA I-treated indeterminate anagen follicle in longitudinal section from balding scalp showing minimal UEA I positivity (single arrow) of the portion of the follicles situated below the dermosubcutaneous junction;

FIG. 2(b) is a photomicrograph at 400× magnification of a UEA I-treated indeterminate anagen follicle in cross-section from balding scalp showing some UEA I positivity of the internal root sheaths (single arrow) and minimal or no staining of the keratinocytes of the external root sheaths (E);

FIG. 3 is a photomicrograph at 250× magnification of a UEA I-treated anagen hair follicle following new hair regrowth in oblique section showing UEA I positivity of the infrainfundibular follicular keratinocytes of the external root sheaths (E) and internal root sheaths (I);

FIG. 4 shows a comparison of the percentage of UEA I positivity of the infrainfundibular follicular keratinocytes of terminal scalp, vellus, and balding follicles (untreated and after new hair regrowth) in the anagen and telogen phases, with results expressed as mean ±SE;

FIG. 5(a) is a photomicrograph at 400× magnification of a UEA I-treated vellus forearm anagen follicle in longitudinal section through the bulb showing minimal UEA I positivity of external (single arrow) and internal root sheaths (double arrows) and showing weak UEA I staining compared to the blood vessels;

FIG. 5(b) is a photomicrograph at 400× magnification of a UEA I-treated vellus forearm anagen follicle showing the suprabulbar portion, showing minimal UEA I positivity of the follicular keratinocytes of the internal root sheaths (single arrows) but no staining of the internal root sheaths (E), in which the weakness of the UEA I binding can be compared with the UEA I positivity of the perifollicular blood vessels (double arrows); and FIG. 6 shows a comparison of the length of the infrainfundibular follicle in millimeters in terminal scalp, balding scalp (untreated and after new hair regrowth), and vellus follicles, with results being expressed as mean ±SE.

DESCRIPTION

I. Introduction

I have developed a method of distinguishing active from inactive hair follicles and determining the effectiveness of a potential antibaldness medication. This method is based on the discovery that the infrainfundibular portion of the cell membrane of the keratinocytes of active hair follicles in the human scalp has L-fucose on its surface and can bind a lectin specific for that sugar. The invention comprises this method, as well as a kit for performing tests according to the method.

Active scalp hair follicles in the human scalp, designated terminal follicles, undergo a cycle of anagen, catagen, and telogen phases with hair growth active in the anagen phase and inactive in the catagen and telogen phases. In cases of partial male pattern baldness (androgenetic alopecia), more follicles are present in the catagen and telogen phases and fewer in the active anagen phase. Eventually, the follicles are converted into indeterminate follicles, which have only a short growing phase and produce fine hairs with a short overall length, i.e., they have properties similar to those of vellus follicles. Drugs that can reverse baldness, such as minoxidil, are believed to reconvert vellus follicles or indeterminate follicles to terminal follicles having a substantially longer anagen phase.

Thus, a specific marker for the active anagen phase of terminal hair follicles would serve as a indicator of the effectiveness of an antibaldness medication in reconverting largely inactive vellus or indeterminate follicles to the active terminal type.

I have determined the six-carbon sugar L-fucose represents such a marker for the active anagen phase of terminal follicles. Hair follicles, lined by keratinocytes, have infundibular and infrainfundibular regions, which can be distinguished by light microscopy of longitudinal sections. In terminal hairs, L-fucose is abundant in the infrainfundibular region of the cell membrane of suprabasal follicular keratinocytes in the anagen phase, decreasing in the catagen phase, and minimal or absent in the telogen phase. The L-fucose moiety is also minimal or absent in vellus follicles. Fucose is a terminal constituent of many carbohydrate chains which form the integral part of many cell-surface glycoproteins. L-fucose is specifically bound by a number of molecules known as lectins including *Ulex europaeus* lectin I; *Lotus tetragonolobus* lectins I, II, and III; and *Anguilla rostrata* lectin.

Terminal hair follicles in the anagen phase of growth can be identified by determining the lectin bound. The lectin preferentially binds to terminal hair follicles in the anagen phase as opposed to terminal hair follicles in phases other than anagen or non-terminal hair follicles.

II. Distinguishing Active from Inactive Hair Follicles

A. Lectin

The lectin can be any lectin capable of specifically binding L-fucose on the infrainfundibular portion of the cell membrane of suprabasal keratinocytes. Such lectins include *Ulex europaeus* lectin I; *Lotus tetragonolobus* lectins I, II, and III; and *Anguilla rostrata* lectin. Preferably, the lectin is *Ulex europaeus* lectin I.

B. Conditions for Binding of the Lectin

The conditions for binding of the lectin to cell membranes are generally noncritical. The binding can be performed at any temperature from about 4° C. to about 37° C.; typically, the binding is performed at ambient temperature. The binding typically occurs at pH 7-8, more typically about pH 7.2-7.8, and can occur in any buffer of ionic strength equivalent to about 250 mM NaCl or less that preserves the activity of the lectin. The time of binding can be from about 10 minutes up to about 2 hours; typically, the binding is carried out from about 20 minutes to about 1 hour. The lectin is typically diluted for binding from an original stock into a buffer in which the lectin is stable. For *Ulex europaeus* lectin I, the optimal dilution is about 1:40.

C. Tissue Samples Used for Binding

Typically, the binding and detection process of the present invention is performed on punch biopsies of scalp tissue. Frozen sections are prepared of these biopsies. Typically, the sections are transferred to microscope slides coated with poly-L-lysine, dried overnight at room temperature, fixed in acetone for 10 minutes, and then allowed to dry thoroughly. The resulting sections are used for lectin binding in vitro.

D. Detection of Lectin Binding

Preferably, the binding of the lectin to the cell membrane of the infrainfundibular portion of the suprabasal keratinocytes is detected through a biotin linker, the lectin being biotinylated. The term "biotinylated" is intended to encompass not only biotin itself, but derivatives of biotin, including derivatives such as $\omega$-caproamidobiotin or other derivatives in which the carboxyl group is bound in amide or ester linkage to a moiety comprised of methylene ($CH_2$) units. The cell membrane to which the lectin is or may be bound is contacted with a label conjugate comprising a substance specific for biotin conjugated to a detectable label. The substance specific for biotin is preferably avidin, but an antibody specific for biotin can also be used.

A detectable label is bound to the avidin or biotin-specific antibody. The label can be a radioactive label, a colorimetric label, a fluorescent label, or an enzyme label. Preferably, the label is an enzyme label. The enzyme label is preferably horseradish peroxidase, but can also be alkaline phosphatase, $\beta$-galactosidase, glucose oxidase, or other enzymes commonly used in enzyme-linked assays.

If an enzyme label is used, it is preferably detected by incubating the enzyme label with a substrate such as diaminobenzidine which, when acted upon by the enzyme, produces an insoluble product marking the location of the label. The incubation typically takes place in a buffer of moderate ionic strength and a pH of 6-9, more typically pH 7-8.5, and at a temperature approximately ambient. Use of such enzyme labels is well known in the art.

The label present on the infrainfundibular region of the cell membrane of suprabasal keratinocytes is then determined by observing it by a technique such as light microscopy, fluorescence microscopy, or autoradiography, depending upon the nature of the label used.

Another aspect of the invention is a kit for the identification of terminal hair follicles in the anagen phase. The kit comprises:

(1) a biotinylated lectin capable of specifically binding L-fucose on the cell membrane of the infrainfundibular portion of suprabasal keratinocytes;

(2) a label conjugate comprising a substance specific for biotin conjugated to a detectable label, the substance specific for biotin being selected from the group consisting of avidin and an anti-biotin antibody; and (3) means for detecting the label.

The means for detecting the label depends on the exact nature of the label used, and can comprise substrates, buffers, enzymes, or means for the autoradiographic detection of radioactivity.

In a less preferred alternative, the lectin itself is conjugated to a detectable label, such as a radioactive label, a fluorescent label, a colorimetric label, or an enzyme label. In this alternative, the lectin is not biotinylated, and a second component such as avidin or an anti-biotin antibody is not used.

III. Method of Determining the Effectiveness of a Drug Potentially Useful for Therapy of Androgenetic Alopecia The present invention also comprises a method of determining the effectiveness of a drug for therapy of androgenetic alopecia. This method is based on the discovery that drugs such as minoxidil and retinoic acid, now known to be useful for the treatment of androgenetic alopecia (male pattern baldness), can reconvert scalp hair follicles from vellus follicles or indeterminate follicles into terminal follicles in the active anagen phase. This reconversion is accompanied by a greatly increased binding of lectins specific for L-fucose to the infrainfundibular region of the cell membrane of the suprabasal keratinocytes of the reconverted follicles.

The effectiveness of a drug for therapy of androgenetic alopecia can be tested either on multiple scalp regions of a single patient or on multiple patients.

If multiple scalp regions of a single patient are used, the method comprises:

(1) selecting a patient an area of whose scalp is affected by androgenetic alopecia;

(2) treating only a first region of the area of the scalp affected by androgenetic alopecia with a known dosage of the drug while leaving a second region untreated;

(3) contacting the cell membrane of the infrainfundibular suprabasal keratinocytes of the first and second regions with a lectin capable of specifically binding L-fucose on the cell membrane of the infrainfundibular keratinocytes; and (4) comparing the binding of the lectin to the infrainfundibular portion of suprabasal keratinocytes in the first and second regions to determine the effectiveness of the drug.

The quantity of lectin bound per suprabasal keratinocyte in the first and second regions can be determined. The difference between the quantity of lectin bound per suprabasal keratinocyte in the first and second regions is a measure of the effectiveness of the drug at the dosage administered in reconverting inactive follicles to active terminal follicles in the anagen phase of growth.

If multiple patients are used, the method comprises:

(1) selecting at least two patients, areas of whose scalps are affected by androgenetic alopecia;

(2) treating a region of the area of the scalp affected by androgenetic alopecia of at least one patient with a known dosage of the drug;

(3) leaving a corresponding region of the area of the scalp affected by androgenetic alopecia of at least one patient untreated;

(4) contacting the cell membrane of the infrainfundibular suprabasal keratinocytes in the region of the scalps of the treated and untreated patients with a lectin capable of specifically binding L-fucose on the cell membrane of the infrainfundibular keratinocytes; and (5) comparing the binding of the lectin to the infrainfundibular suprabasal keratinocytes in the region for treated and untreated patients to determine the effectiveness of the drug at the dosage administered.

IV. Method of Identifying Terminal Follicles by the Length of Their Infrainfundibular Portions The present invention further comprises a method of identifying terminal hair follicles by the length of their infrainfundibular portions. As shown below in Example 3, the length of the infrainfundibular portion of terminal hair follicles is correlated with the phase of growth of the follicles. Terminal follicles in the anagen phase of growth have significantly longer infrainfundibular regions than do terminal follicles in other than the anagen phase of growth or non-terminal follicles. Thus, a comparison of the mean value obtained from the distribution of lengths of the infrainfundibular region of the follicles with values characteristic of terminal follicles in the anagen phase of growth and follicles other than terminal follicles in the anagen phase can identify the follicles as terminal follicles in the anagen phase of growth.

The method comprises:

(1) taking a scalp biopsy from the scalp on which terminal hair follicles in the anagen phase of growth are to be identified;

(2) preparing a longitudinal section from the biopsy;

(3) measuring the length of the infrainfundibular portion of a sufficient number of follicles in the section to obtain a distribution of lengths of the infrainfundibular portion of the follicles and a mean value of the distribution; and (4) comparing the mean value of the distribution of follicle lengths with values characteristic of terminal follicles in the anagen phase and follicles other than terminal follicles in the anagen phase to identify terminal hair follicles in the anagen phase.

The invention is illustrated by the following examples. The examples are for illustrative purposes only and are not to be construed as limiting the scope of the invention in any manner.

EXAMPLE 1—SELECTION AND TREATMENT OF PATIENTS

Twenty-three patients with ages ranging from 28 to 72 years, mean 45 years, were studied. The patients, classified according to Hamilton's classification (Hamilton, "Pattern Loss of Hair in Man: Types and Incidents," *Ann. N.Y. Acad. Sci.* 53, 708–728 (1951)), had androgenetic alopecia ranging in severity from type III to type VI. The patients were randomly assigned to the following treatment groups: (a) minoxidil 0.5%; (b) retinoic acid 0.05%; (c) minoxidil 0.1% with retinoic acid 0.05%; and (d) minoxidil 0.5% with retinoic acid 0.05%. The minoxidil and/or retinoic acid were administered in a liquid preparation comprising mostly propylene glycol. All the patients were initially subjected to punch biopsies of both the bald (frontal or vertex areas) and hairy, occipital (uninvolved, normal) areas of the scalp. The patients were followed up in a dermatology clinic (Veterans' Administration Medical Center, Sepulveda, Calif.) every three to six months. Vellus hairs from forearm biopsies of four patients served as controls.

Two 4-mm punch biopsies were taken from each of the bald and normal scalps from all 23 patients before therapy and from areas of new terminal hair regrowth (moderate regrowth) in three patients. Biopsies were also taken from treated bald areas which failed to grow hair in six patients. The biopsies were processed for light microscopy (Example 3) and lectin studies (Example 4).

EXAMPLE 2—LIGHT MICROSCOPIC ANALYSIS OF RESULTS

The 4-mm punch biopsies (Example 1) were taken and divided longitudinally. One-half was fixed in 10% neutral buffered formalin and processed for light microscopy. Paraffin sections were stained with hematoxylin and eosin and examined under a light microscope. Forty-two biopsies (excluding those from two patients who dropped from the study) were processed for baseline studies, with 21 biopsies taken from bald/balding areas and 21 biopsies from uninvolved scalp (occipital areas). Four sections were saved from each biopsy.

Longitudinal sections of hair follicles were measured in all biopsies, using paraffin section stain with hematoxylin and eosin. The follicles were photographed at 40× magnification, focusing on the infrainfundibular portions between the sebaceous duct/follicular junction in the hair bulb, using slightly overlapping photomicrographs printed out at 2.5× magnification. The length of the follicles between the sebaceous duct/follicle junction and the tip of the bulb was then measured and the data corrected for the total magnification by dividing by 100.

The following criteria for anagen and telogen follicles were used. Anagen follicles have the following characteristics on light microscopy: (1) the bulbar portions of the follicles are well developed; (2) the follicles contain a well-developed hair shaft, which is connected to the bulbar epithelium; (3) the infrainfundibular portions of the follicle are greater in length than the infundibular portions of the follicle; and (4) there is no crimping of the bulbar portions of the follicle as seen in early telogen. Telogen follicles, on the other hand, have the following characteristics: (1) the bulbar portions of the follicles are small and underdeveloped; (2) there is nearly always (more than 95%) no hair shaft within the follicle; and (3) the infrainfundibular portions of the follicle are nearly always shorter in length than the infundibular follicle, with the exception of follicles in early telogen, which are recognized, in turn, by the crimped appearance of the bulbar epithelium.

Indeterminate follicles were seen in balding scalps. These possess features intermediate between terminal and vellus follicles, but more closely resemble the latter. The intermediate follicles in the anagen phase were smaller than terminal follicles in the anagen phase, with the smaller bulbar portions situated either above or below dermosubcutaneous junctions. The telogen phase of these follicles resembled their vellus counterpart.

EXAMPLE 3—ANALYSIS OF RESULTS WITH LECTIN

Adjacent 4-mm punch biopsies were taken for lectin studies. These were imbedded in OCT compound (Tissue-Tek, Baxter Scientific, Morton Grove, Ill.), snap-frozen in liquid nitrogen, and stored at −70° C. Cryostat sections were prepared on poly-L-lysine coated slides, dried overnight at room temperature, fixed in acetone at room temperature for 10 min, and allowed to dry thoroughly. The sections were then incubated with dilutions of various biotinylated lectins, as shown in Table I, from Vector Laboratories, Inc. (Burlingame, Calif.). The resultant sections were then processed using Vectastain ™ IgG ABC kit (Vector Laboratories), and labeled with diaminobenzidine.

TABLE I

| Lectin Dilution | Sugar Specificity | |
|---|---|---|
| Concanavalin A | Glucose, mannose | 1:40 |
| Peanut agglutinin | β-D-galactose | 1:40 |
| Ulex europaeus agglutinin I (UEA I) | L-fucose | 1:80 |
| Wheat germ agglutinin 1:400 | N-acetyl-glucosamine | |

Longitudinal sections of the frozen biopsies processed for *Ulex europaeus* lectin I (UEA I) binding were measured for percentage of binding by infrafollicular keratinocytes as follows: The lectin-stained sections were photographed at a magnification of 40× and printed at a further magnification of 2.5×, using slightly overlapping photomicrographs. The surface areas of UEA I positive keratinocytes and UEA I negative keratinocytes were then determined by means of a graphics tablet connected to a microcomputer, and their percentages were calculated. Only the sections involving the bulb and suprabulbar regions were measured. Cross-sections of the bulbar and suprabulbar areas of the follicles were also measured in some patients. The data utilizing these sections was found not to differ significantly from that obtained from longitudinal sections.

The most significant differences between the bald and occipital scalp biopsies as well as between the occipital scalp follicles and vellus follicles of the forearm were noted with studies employing the UEA I lectin.

SCALP BIOPSY RESULTS

In biopsies from uninvolved (occipital) scalp, the UEA I lectin, which has L-fucose specificity, was observed to bind strongly to the surface plasma membrane of the infrainfundibular follicular keratinocytes (91.8%±3.1%; mean ±SE) of the anagen follicles (terminal hair follicles) from early anagen (FIG. 1(a)) to the more established follicles of anagen hairs situated just above (FIG. 1(b)) or below (FIG. 1(c)) the dermosubcutaneous junction. However, in terminal hairs undergoing early catagen, recognized by the crimping of the internal root sheaths (FIG. 1(d)), the follicular keratinocytes of the external root sheaths were the first to lose the L-fucose moiety. This demonstrated by loss of UEA I binding on follicular keratinocytes of the external root sheaths (FIG. 1(e)). This alternation in UEA I binding sites occurs prior to a decrease in perifollicular vascularity (FIG. 1(c)). Well-established telogen follicles of occipital scalp, however showed minimal (4.0%±0.8%) UEA I positivity (FIG. 1(e)).

By contrast, in biopsies from completely bald scalps (20/23 patients), the only follicles present were telogen follicles, which showed no staining with UEA I lectin in their infrainfundibular portions. (There was usually variable UEA I positivity of infundibular portions of the follicles in occipital, balding (indeterminate), and vellus forearm follicles.) Even the anagen follicles situated below the dermosubcutaneous junction (FIGS. 2(a), 2(b)) in balding scalps revealed minimal binding (FIGS. 2(a), 2(b)) of the infrainfundibular follicular keratinocyte epithelium to UEA lectin compared with anagen phase terminal hairs of occipital scalp (FIGS. 1(b), 1(c)), with the less affected scalps revealing more UEA I positivity than the more affected scalps. The telogen follicles of balding scalps showed little or no UEA I staining (1.8%±0.5%).

In biopsies from areas of new hair regrowth (three patients) after treatment with hair growth promoters such a retinoic acid and/or minoxidil, it was noted that UEA I lectin binding sites were increased (80.6%±6.1%) in the anagen follicles, with the lectin binding strongly to the infrainfundibular follicular keratinocytes (FIG. 3). This increase in UEA I binding was not observed in the six patients in whom visible hair regrowth was not noted by both patient an investigator. This suggested UEA I binding can be used as a marker to assess the effectiveness of drugs or treatments potentially useful for the treatment of male pattern baldness as a rapid alternative to manual hair-counting methods. Telogen follicles in all patients showed minimal (FIG. 4) UEA I positivity.

VELLUS CONTROL (FOREARM) BIOPSIES

In the vellus follicles of the forearm, the anagen hairs revealed decreased (23.2%±6.3%) UEA I positive (FIGS. 4(a), 4(b)) infrainfundibular follicular keratinocytes with much weaker staining than that noted in the terminal follicles. Telogen vellus follicles revealed minimal (1.9%±0.2%) UEA I positivity.

CORRELATION BETWEEN UEA POSITIVITY AND HAIR CYCLE

A positive correlation between the percentage UEA I positivity and the anagen phase of the hair cycle was noted for terminal occipital scalp hairs, indeterminate hairs of balding scalps, and vellus forearm hairs (FIG. 5). In addition, UEA I positivity of 91.8%±3.1% in anagen phase terminal hairs was significantly different ($p<0.001$) from the UEA I positivity of 28.5%±5.2% noted in the anagen phase hairs of balding scalps. On the other hand, there was no significant difference ($p>0.05$) between the UEA I positivity of the balding scalp (28.5%±5.2%) and vellus forearm hairs (23.2%±6.3%) (FIG. 4). The UEA I positivity of the new hair regrowth after therapy with hair promoters such as minoxidil and/or retinoic acid tends to resemble that of terminal hairs rather than vellus hairs (FIG. 4). These findings show that UEA I positivity of the infrainfundibular portion of the plasma membrane of suprabasal keratinocytes is a useful marker for the proliferative phase in the hair cycle. The loss of UEA I binding by the infrainfundibular keratinocytes may mark the loss of proliferative activity in the hair follicles of the scalp.

CORRELATION BETWEEN LENGTH OF INFRAINFUNDIBULAR FOLLICLES AND HAIR CYCLE

The length of the infrainfundibular portion of the follicles also correlated with the anagen phase of the hair cycle in all hair types (FIG. 6), being much longer in the anagen than in the telogen follicles. Again the results were significantly different between the terminal hairs (3.4±0.5 mm) of occipital scalp and indeterminate hairs (1.7±0.6 mm) of balding scalp ($p<0.01$), but not significantly different ($p>0.05$) between the indeterminate hairs (1.7±0.6 mm) and vellus hairs (1.5±0.4 mm) (FIG. 6). In the three patients with hair regrowth, there was an increase in the length of the infrainfundibular follicle region (FIG. 6).

ADVANTAGES OF THE INVENTION

The present invention provides a rapid and accurate method of determining the effectiveness of a prospective anti-baldness medication. The simplicity of this method coupled with the freedom from having to count large numbers of hairs manually, makes it possible not only to screen a large number of prospective anti-baldness drugs, but also to establish the optimal dose for administration for drugs shown to have some activity by preliminary screening. Because the method of the present invention is likely to be directly related to the differentiation of the keratinocytes themselves, it is highly reliable in assessing the effect of such drugs or medications upon hair growth. It requires relatively little equipment and can be practiced using readily available materials.

Although the present invention has been described in considerable detail with reference to certain preferred versions thereof, other versions are possible. Therefore, the spirit and scope of the appended claims should not be limited to the description of the preferred versions contained herein.

What is claimed is:

1. A method for identifying terminal hair follicles in the anagen phase of growth in the human scalp, the follicles having suprabasal keratinocytes which have distinguishable infundibular and infrainfundibular portions, the method comprising the steps of:

(a) contacting the cell membrane of the infrainfundibular portion of the suprabasal keratinocytes with a lectin capable of specifically binding to L-fucose on the cell membrane of the infrainfundibular portion of the suprabasal keratinocytes; and (b) identifying the terminal hair follicles by determining the lectin so bound to the L-fucose on the cell membrane of the infrainfundibular portion of the suprabasal keratinocytes, the lectin preferentially binding to terminal hair follicles in the anagen phase of growth as opposed to terminal hair follicles in phases of growth other than anagen or non-terminal hair follicles.

2. The method of claim 1 wherein the lectin is selected from the group consisting of *Lotus tetragonolobus* lectin I, *L. tetragonolobus* lectin II, *L. tetragonolobus* lectin III, *Ulex europaeus* lectin I, and *Anguilla rostrata* lectin.

3. The method of claim 2 wherein the lectin is *Ulex europaeus* lectin I.

4. The method of claim 1 wherein the lectin is biotinylated and the step of determining the lectin bound comprises contacting the cell membrane with a label conjugate comprising a substance specific for biotin conjugated to a detectable label, the substance specific for biotin being selected from the group consisting of avidin and an anti-biotin antibody.

5. The method of claim 4 wherein the substance specific for biotin is avidin.

6. The method of claim 5 wherein the detectable label is selected from the group consisting of radioactive labels, fluorescent labels, colorimetric labels, and enzyme labels.

7. The method of claim 6 wherein the detectable label is an enzyme label.

8. The method of claim 7 wherein the enzyme label is horseradish peroxidase.

9. The method of claim 1 wherein the lectin is conjugated to a detectable label, the detectable label being selected from the group consisting of radioactive labels, fluorescent labels, colorimetric labels, and enzyme labels.

10. A method for determining the effectiveness of a drug for therapy of androgenetic alopecia, the method comprising the steps of:

(a) selecting a patient whose scalp is affected by androgenetic alopecia;

b) treating a first region of the area of the scalp affected by androgenetic alopecia with a known dosage of the drug while leaving a second region untreated;

(c) contacting the cell membrane of the infrainfundibular portion of the suprabasal keratinocytes of the first and second regions of step (b) with a lectin capable of specifically binding L-fucose on the cell membrane of the infrainfundibular portion of the suprabasal keratinocytes; and (d) comparing the binding of the lectin to the infrainfundibular portion of the suprabasal keratinocytes in the first and second regions to determine the effectiveness of the drug at the dosage administered.

11. The method of claim 10, wherein the step of comparing the binding of the lectin to the infrainfundibular portion of the suprabasal keratinocytes in the first and second regions comprises determining the quantity of lectin bound per suprabasal keratinocyte in the first and second regions, the difference between the quantity of lectin bound per suprabasal keratinocyte in the first and second regions being a measure of the effectiveness of the drug.

12. The method of claim 10 wherein the lectin is selected from the group consisting of *L. tetragonolobus* lectin I, *L. tetragonolobus* lectin II, *L. tetragonolobus* lectin III, *Ulex europaeus* lectin I, and *Anguilla rostrata* lectin.

13. The method of claim 12 wherein the lectin is *Ulex europaeus* lectin I.

14. The method of claim 1 wherein the lectin is biotinylated and the step of comparing the lectin bound in the first and second regions comprises contacting the cell membrane with a label conjugate comprising a substance specific for biotin conjugated to a detectable label, the substance specific for biotin being selected from the group consisting of avidin and an anti-biotin antibody.

15. The method of claim 14 wherein the substance specific for biotin is avidin.

16. The method of claim 10 wherein the lectin is conjugated to a detectable label, the detectable label being selected from the group consisting of radioactive labels, fluorescent labels, colorimetric labels, and enzyme labels.

17. A method for determining the effectiveness of a drug for therapy of androgenetic alopecia, the method comprising the steps of:
   (a) selecting at least two patients whose scalps are affected by androgenetic alopecia;
   (b) treating a region of the area of the scalps affected by androgenetic alopecia of at least one patient with a drug at a known dosage;
   (c) leaving a corresponding region of the area of the scalp unaffected by androgenetic alopecia of at least one patient untreated;
   (d) contacting the cell membrane of the infrainfundibular portion of the suprabasal keratinocytes in the region of the scalps of the treated and untreated patients with a lectin capable of specifically binding L-fucose on the cell membrane of the infrainfundibular portion of the keratinocytes; and
   (e) comparing the binding of the lectin to the infrainfundibular portion of the suprabasal keratinocytes in the region for treated and untreated patients to determine the effectiveness of the drug at the dosage administered.

18. The method of claim 17, wherein the step of comparing the binding of the lectin to the infrainfundibular portion of the suprabasal keratinocytes in the region of the scalps of the treated and untreated patients comprises determining the quantity of lectin bound per suprabasal keratinocyte in the region of the scalp in the treated and untreated patients, the difference between the quantity of lectin bound per suprabasal keratinocyte in the treated and untreated patients being a measure of the effectiveness of the drug.

19. The method of claim 17 wherein the lectin is selected from the group consisting of *L. tetragonolobus* lectin I, *L. tetragonolobus* lectin II, *L. tetragonolobus* lectin III, *Ulex europaeus* lectin I, and *Anguilla rostrata* lectin.

20. The method of claim 19 wherein the lectin is *Ulex europaeus* lectin I.

21. The method of claim 17 wherein the lectin is biotinylated and the step of comparing the lectin bound in the treated and untreated patients comprises contacting the cell membrane with a label conjugate comprising a substance specific for biotin conjugated to a detectable label, the substance specific for biotin being selected from the group consisting of avidin and an anti-biotin antibody.

22. The method of claim 21 wherein the substance specific for biotin is avidin.

23. The method of claim 17 wherein the lectin is conjugated to a detectable label, the detectable label being selected from the group consisting of radioactive labels, fluorescent labels, colorimetric labels, and enzyme labels.

* * * * *